(12) United States Patent
Castelli et al.

(10) Patent No.: US 7,317,127 B2
(45) Date of Patent: Jan. 8, 2008

(54) PROCESS FOR THE OPTICAL RESOLUTION AND RECYCLING OF TOMOXETINE

(75) Inventors: Eugenio Castelli, Arlate di Calco (IT); Giuseppe Lo Monaco, Seregno (IT); Silvia Mantovani, Cesano Maderno (IT); Paola Daverio, Villasanta (IT); Paolo Riva, Monza (IT); Alessandra Vailati, Seregno (IT); Stefano Bianchi, Como (IT)

(73) Assignee: Teva Pharmaceutical Fine Chemicals S.r.l, Petah Tiqva (IL)

( * ) Notice: Subject to any disclaimer, the term of this patent is extended or adjusted under 35 U.S.C. 154(b) by 228 days.

(21) Appl. No.: 11/170,379

(22) Filed: Jun. 28, 2005

(65) Prior Publication Data

US 2006/0009530 A1  Jan. 12, 2006

Related U.S. Application Data

(60) Provisional application No. 60/690,738, filed on Jun. 14, 2005, provisional application No. 60/689,778, filed on Jun. 9, 2005, provisional application No. 60/675,369, filed on Apr. 26, 2005, provisional application No. 60/666,666, filed on Mar. 30, 2005, provisional application No. 60/652,332, filed on Feb. 11, 2005, provisional application No. 60/652,331, filed on Feb. 11, 2005, provisional application No. 60/652,330, filed on Feb. 11, 2005, provisional application No. 60/622,065, filed on Oct. 25, 2004, provisional application No. 60/609,716, filed on Sep. 14, 2004, provisional application No. 60/583,644, filed on Jun. 28, 2004, provisional application No. 60/583,643, filed on Jun. 28, 2004, provisional application No. 60/583,641, filed on Jun. 28, 2004.

(51) Int. Cl.
C07C 209/88 (2006.01)
A61K 31/135 (2006.01)
C07B 57/00 (2006.01)

(52) U.S. Cl. ............... 564/425; 564/303; 564/424; 514/649

(58) Field of Classification Search .......... None
See application file for complete search history.

(56) References Cited

U.S. PATENT DOCUMENTS 4,018,895 A   4/1977  Molloy et al.
4,777,291 A  10/1988  Misner
4,868,344 A   9/1989  Brown
5,658,590 A   8/1997  Heiligenstein et al.
6,333,198 B1 12/2001  Edmeades et al.
6,541,668 B1  4/2003  Kjell et al.

FOREIGN PATENT DOCUMENTS

| DE | 41 23 253 A1 | 1/1993 |
|---|---|---|
| EP | 0 052 492 A1 | 5/1982 |
| EP | 0 193 405 A1 | 9/1986 |
| EP | 0 721 777 A2 | 1/1995 |
| WO | WO 94/00416 | 1/1994 |
| WO | WO 00/58262 | 10/2000 |
| WO | WO 00/64855 | 11/2000 |
| WO | WO 2006/004923 A2 | 1/2006 |
| WO | WO 2006/004976 A2 | 1/2006 |
| WO | WO 2006/004979 A2 | 1/2006 |
| WO | WO 2006/020348 A2 | 2/2006 |
| WO | WO 2006/068662 A1 | 6/2006 |

OTHER PUBLICATIONS

Srebnik, M. et al. "Chiral Synthesis via Organoboranes. 18. Selective Reductions. 43. Dissopinocampheylchloroborane as an Excellent . . . " J. Org. Chem. (1988), vol. 53, p. 2916-2920.
ANON (R)-(−)-N-Methyl-3-(2-Methylphenoxy)Phenyl-3-Phenylpropylamine (S)-(+)-Mandelate Chemical Abstracts Service XP-002367856 Dec. 29, 2004.
Koenig, T.M. et al. "A Convenient Method for Preparing Enantiomerically Pure Norfluoxetine, Fluoxetine and Tomoxetine" Tetrahedron Letters, vol. 35, No. 0, pp. 1339-1342 (1994).
Strobel, H.A.; Heineman, W.R., Chemical Instrumentation: A Systematic Approach, 3rd dd. (Wiley & Sons: New York 1989)—pp. 391-393, 879-894, 922-925, 953.
Snyder, L.R.; Kirkland, J.J., Introduction to Modern Liquid Chromatography, 2nd ed. (John Wiley & Sons: New York 1979)—p. 549-552, 571-572.
Sellers, J.A. et al. "Determination of the Enantiomer and Positional Isomer Impurities in Atomoxetine Hydrochloride with Liquid Chromatography Using Polysaccharide Chiral Stationary Phases." *J. of Pharmaceutical and Biomedical Analysis*, vol. 41, pp. 1088-1094 (2006).

*Primary Examiner*—Brian Davis
(74) *Attorney, Agent, or Firm*—Kenyon & Kenyon LLP

(57) ABSTRACT

The present invention provides a process for the optical resolution of racemic tomoxetine under reaction conditions that improve reaction yields and optical purity. The invention also provides an epimerization process for the (S)-(+) enantiomer. The invention further provides the conversion of the enantiomer obtained from the optical resolution into atomoxetine or a pharmaceutically acceptable salt thereof.

26 Claims, No Drawings

PROCESS FOR THE OPTICAL RESOLUTION AND RECYCLING OF TOMOXETINE

CROSS-REFERENCE TO RELATED APPLICATIONS

This application claims the benefits of U.S. Provisional Patent Application Nos. 60/583,641, filed Jun. 28, 2004, 60/609,716, filed Sep. 14, 2004, 60/622,065, filed Oct. 25, 2004, 60/652,330, filed Feb. 11, 2005, 60/583,644, filed Jun. 28, 2004, 60/652,332, filed Feb. 11, 2005, 60/583,643, filed Jun. 28, 2004, 60/652,331, filed Feb. 11, 2005, 60/666,666, filed Mar. 30, 2005, 60/675,369, filed Apr. 26, 2005, Application Ser. No. 60/689,778, filed Jun. 9, 2005, and Application Ser. No. 60/690,738, filed Jun. 14, 2005, the contents of all of which are incorporated herein by reference.

FIELD OF THE INVENTION

The present invention relates to a process for optical resolution of racemic tomoxetine. The present invention also relates to a process for recycling of (S)-(+)-tomoxetine.

BACKGROUND OF THE INVENTION

Atomoxetine HCl is a selective norepinephrine reuptake inhibitor. It is marketed under the name STRATTERA® for the treatment of Attention-Deficit/Hyperactivity Disorder (ADHD) and is available in 10 mg, 18 mg, 25 mg, 40 mg, and 60 mg dosage forms. It is a white to practically white solid, which has a solubility of 27.8 mg/ml in water.

Atomoxetine, chemically known as (R)(−)-N-methyl-3-(2-methylphenoxy)-3-phenylpropylamine, has the following structure:

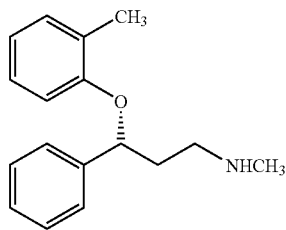

Atomoxetine, the (R)-(−) enantiomer of tomoxetine, is an aryloxyphenylpropylamine. It is about twice as effective as the racemic mixture and about nine times more effective than the (+)-enantiomer, as disclosed in U.S. Pat. No. 4,018,895 (assigned to Eli Lilly and Co.), EP 0 052 492 (Eli Lilly and Co.), and EP 0 721 777 (Eli Lilly and Co.).

Several processes for synthesizing 3-aryloxy-3-phenylpropylamines are known in the art. For example, U.S. Pat. No. 4,018,895 assigned to Eli Lilly and Co. discloses an aliphatic nucleophilic displacement of N-protected-3-halogen-3-phenylpropylamines by phenols, followed by N-deprotection. U.S. Pat. No. 4,868,344 assigned to Aldrich-Boranes, Inc. relates to the Mitsunobu reaction between 3-hydroxy-3-phenylpropylhalides and phenols, followed by amination of the resulting 3-aryloxy-3-phenylpropylhalides. Tomoxetine is also synthesized by the processes disclosed in U.S. Pat. No. 6,541,668, and WO 00/58262 assigned to Eli Lilly and Co. and WO 94/00416 by Richter Gedeon Vegyeszeti Gyar RT. These patents disclose an aromatic nucleophilic displacement of an aryl halide by 3-hydroxy-3-phenylpropylamines under strongly basic conditions. The nucleophilic aromatic displacement process disclosed in WO 00/58262 comprises reacting N-methyl-3-hydroxy-3-phenylpropylamine with a protected 2-fluoroberizaldehyde to produce tomoxetine after several functional group interconversion steps.

Optical resolution of racemic tomoxetine into (R)-(−)-tomoxetine (atomoxetine) and (S)-(+)-tomoxetine is known in the art. Common techniques include chiral chromatography and fractional crystallization of (S)-(+)-mandelic acid diastereoisomeric addition salts. Because the former is more costly and not optimized for large scale synthesis, the latter is preferred for commercial processes.

EP Patent No. 0 052 492 discloses a process wherein racemic tomoxetine, prepared from N-methyl-3-hydroxy-3-phenylpropylamine, is resolved with (S)-(+)-mandelic acid to obtain (R)-(−)-tomoxetine (S)-(+)-mandelate salt. This process produces a poor yield of about 18%. This process is inefficient and also requires solvents which may be harmful to the environment, such as diethyl ether and dichloromethane. U.S. Pat. No. 6,541,668, assigned to Eli Lilly and Co., discloses an improved resolution process having fewer steps. This process also yields approximately 18% (R)-(−)-tomoxetine (S)-(+)-mandelate (prepared from N-methyl-3-hydroxy-3-phenylpropylamine). However, the optical purity of the (R)-(−)-tomoxetine product is not disclosed.

The poor yields indicate that, in the solvents used, a large amount of the racemic tomoxetine may be unrecovered as (S)-(+)-tomoxetine, the unwanted enantiomer. U.S. Pat. No. 4,777,291, assigned to Eli Lilly and Co., discloses a racemization process from (S)-(+)-tomoxetine to racemic tomoxetine by means of alkyl-alkali metals or alkylamide-alkali metals in tetrahydrofuran or 1,2-dimethoxyethane, preferably butyllithium in tetrahydrofuran. This process requires hazardous solvents and bases unsuitable in a large scale commercial synthesis. Moreover, the patent discloses and one of skill in the art appreciates, that anhydrous media are required in this process.

Epimerizing bases other than alkyl-alkali metals or alkylamide-alkali metals are known in the art for 3-aryloxy-3-phenylpropylamines other than tomoxetine. For example, WO 00/64855 (Eli Lilly and Co.) discloses a racemization process of (S)-fluoxetine into racemic fluoxetine involving a base having a potassium counter-ion in an aprotic highly dipolar solvent.

There is a need in the art for additional processes for optical resolution of racemic tomoxetine in higher yields that can be utilized in large-scale commercial operations. Furthermore, there is also a need for more efficient processes for the epimerization of the unwanted (S)-(+)-enantiomer of tomoxetine.

SUMMARY OF THE INVENTION

The present invention provides a process for the optical resolution of racemic tomoxetine under reaction conditions that improve reaction yields and/or optical purity. The invention also provides an epimerization process of the unwanted (S)-(+) enantiomer.

Thus, in one aspect, the present invention provides a process for the optical resolution of racemic tomoxetine comprising:

a) providing a mixture of tomoxetine racemate, a $C_{1-4}$ alcohol, an aromatic solvent, and (S)-(+)-mandelic acid, b) heating the mixture to a temperature of about 60° C. to about 80° C.; and c) crystallizing (R)-(−)-tomoxetine (S)-(+)-mandelate from the reaction mixture.

In another aspect, the present invention provides a process for optical resolution of racemic tomoxetine comprising:
a) combining, at a temperature of about 40° C. to about 60° C., (S)-(+)-mandelic acid in an aqueous basic solution, tomoxetine racemate, an aromatic solvent and acetic acid, to obtain a mixture;
b) maintaining the mixture for at least one hour to obtain (R)-(−)-tomoxetine (S)-(+)-mandelate; and
c) recovering (R)-(−)-tomoxetine (S)-(+)-mandelate from the reaction mixture.

In yet another aspect, the present invention provides a process for recycling of (S)-(+)-tomoxetine by epimerization. This process comprises:
a) providing a mixture of (S)-(+)-tomoxetine, an aprotic dipolar solvent and a base having a highly ionic counter ion,
b) heating the mixture to a temperature of about 80° C. to about 150° C., and
c) maintaining the mixture for at least 3 hours to obtain racemic tomoxetine.

The racemate may further be optically resolved into the desired (R)-(−)-tomoxetine by the process described above, or by any methods known in the art, e.g., crystallizing (R)-(−)-tomoxetine (S)-(+)-mandelate from the reaction mixture.

In a further aspect, the present invention comprises the preparation of atomoxetine or a pharmaceutically acceptable salt thereof by converting the R(−)-tomoxetine S-(+)-mandelate prepared above to atomoxetine or a pharmaceutical acceptable salt thereof.

Preferably, the pharmaceutically acceptable salt is atomoxetine hydrochloride.

DETAILED DESCRIPTION OF THE INVENTION

As used herein the term "aromatic solvent" refers to a $C_{6-10}$ aromatic hydrocarbon, such as but not limited to, benzene, xylene, or toluene.

The present invention provides processes for the optical resolution of racemic tomoxetine, obtained, for example, according to the process described in U.S. Pat. No. 6,541,668, under reaction conditions that are expected to improve reaction yields and/or optical purity from processes in the prior art.

It is believed that the processes of the present invention have several advantages over the prior art: they do not require distillation of toluene, which is necessary in the process disclosed in U.S. Pat. No. 6,541,668; they avoid anhydrous media and solvents that may be harmful to the environment, which are required in the processes disclosed in EP 0 052 492 and U.S. Pat. No. 4,777,291. Using more environmentally compatible materials is also believed to facilitate large-scale commercial production.

In one embodiment, the process provided by the present invention comprises combining racemic tomoxetine, a $C_{1-4}$ alcohol, and an aromatic solvent. Preferably, the $C_{1-4}$ alcohol is methanol. A preferred aromatic solvent is toluene. Preferably, the $C_{1-4}$ alcohol is combined in an amount of about 0.1 ml per 1 g of the tomoxetine racemate. (S)-(+)-mandelic acid is then added to the racemic tomoxetine solvent mixture. The mixture is heated to a temperature of about 60° C. to about 80° C., which induces dissolution. Preferably, the mixture is heated to a temperature of about 65° C. to about 70° C. After all solids have dissolved, (R)-(−)-tomoxetine (S)-(+)-mandelate is recovered, preferably by crystallization at a temperature of about −5° C. to about 20° C. More preferably, (R)-(−)-tomoxetine (S)-(+)-mandelate is recovered at a temperature of about 0° C.

In another embodiment, the present invention provides a process for optical resolution of racemic tomoxetine in a biphasic system. This process comprises combining tomoxetine racemate with an aqueous solution of (S)-(+)-mandelic acid and a base, in the presence of acetic acid and an aromatic solvent, preferably toluene. The base may be any one of sodium, potassium, cesium, calcium and ammonium hydroxide. More preferably the base is sodium hydroxide. The mixture is then heated to a temperature of about 40° C. to about 60° C. until dissolution occurs, then cooled to a temperature of about −5° C. to about 20° C., and maintained for a sufficient time to bring about the crystallization of (R)-(−)-tomoxetine (S)-(+)-mandelate. Preferably, the mixture is cooled to a temperature of about 0° C.

In another embodiment, the obtained (R)-(−)-tomoxetine (S)-(+)-mandelate salt may be recrystallized from a solution comprising an aromatic solvent and a $C_{1-4}$ alcohol. Preferably, the mixture is heated to a temperature of about 60° C. to about 80° C., more preferably to a temperature of about 65° C. to about 70° C., until all solids dissolve. The obtained solution is then cooled to a temperature from about −5° C. to about 20° C., at which (R)-(−)-tomoxetine (S)-(+)-mandelate recrystallizes. More preferably, the solution is cooled to about 0° C. Preferably, the $C_{1-4}$ alcohol is added in an amount of about 0.6 ml per 1 g of the (R)-(−)-tomoxetine (S)-(+)-mandelate salt. Preferably, the $C_{1-4}$ alcohol is methanol. A preferred aromatic solvent is toluene.

The yield of (R)-(−)-tomoxetine (S)-(+)-mandelate, prepared from N-methyl-3-hydroxy-3-phenylpropylamine, by the process of the present invention is expected to be at least about 35%.

(R)-(−)-tomoxetine (S)-(+)-mandelate may be separated from the reaction mixture by techniques known in the art, such as filtration. The product may be washed with an organic solvent. The product may then be dried, preferably under reduced pressure.

The present invention further provides an improved process for recycling the undesired (S)-(+)-tomoxetine, which is obtained after the optical resolution of the tomoxetine racemate, into the desired (R)-(−) enantiomer. This process comprises racemization of the (S)-(+)-tomoxetine by combining it with an aprotic dipolar solvent, and a base having a highly ionic counter ion, followed by heating of the mixture. Preferably, the mixture is heated to a temperature of about 80° C. to about 150° C., most preferably, the mixture is heated to a temperature of about 85° C. to about 90° C. Preferably, the solvent and base are each added in an amount of at least 2 moles per mole (S)-(+)-tomoxetine. Preferably, the aprotic dipolar solvent is selected from the group consisting of DMF, dimethylacetamide, 1,3-dimethyl-2-imidazolinone and dimethylsulfoxide (DMSO). Most preferably, the aprotic dipolar solvent is DMSO. A preferred base is potassium hydroxide.

The reaction is followed by observing the optical rotation of the mixture. The reaction is complete when the optical rotation of the mixture decreases to 0.00. The duration of the reaction is approximately 3 hours. An organic solvent and water are then added to produce a 2-phase system, and following phase separation, racemic tomoxetine is recovered from the organic phase, preferably by concentration to a residue.

The process provided in the present invention may be depicted as follows:

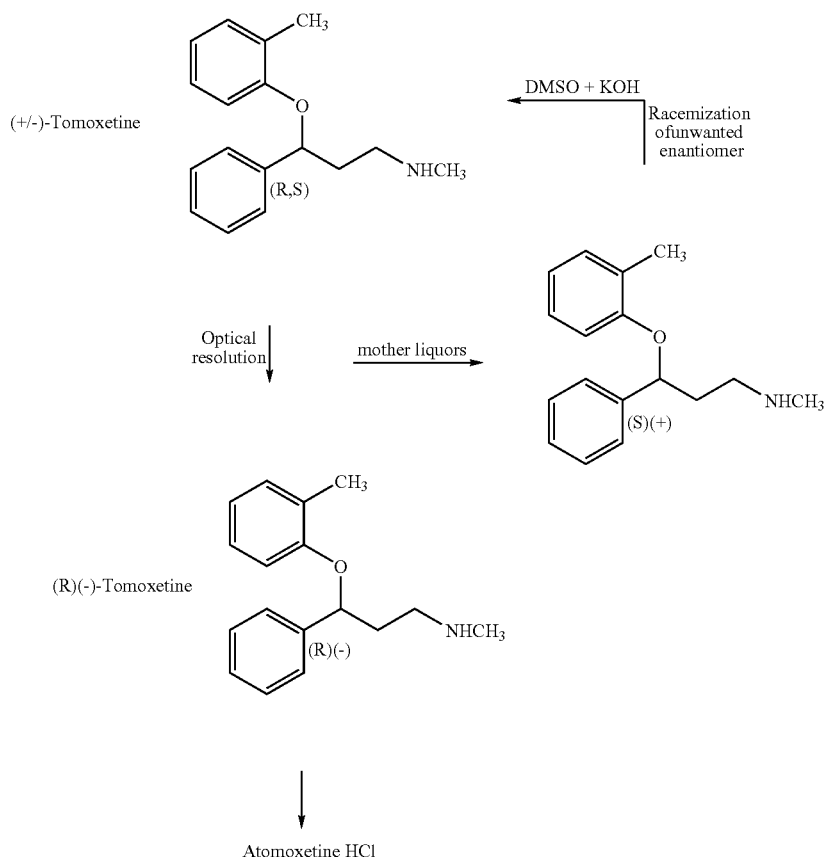

The solvent mixture ("mother liquor") containing the (S)-(+)-tomoxetine that remains following the optical resolution of racemic tomoxetine may be concentrated, preferably under vacuum, in order to decrease reaction time. The term "vacuum," as commonly known in the art, refers to a pressure of less than one atmosphere.

The racemic tomoxetine prepared by this recycling process may then be optically resolved to yield (R)-(−)-tomoxetine (S)-(+)-mandelate, by the processes described above, or by any other methods known in the art.

By epimerizing the unwanted (S)-(+) enantiomer, the atomoxetine yield is increased, and the amount of the reagents wasted during the preparation of atomoxetine is substantially reduced.

In a further embodiment, R(−)-tomoxetine S-(+)-mandelate prepared above is converted into atomoxetine or a pharmaceutically acceptable salt thereof. Preferably, the pharmaceutically acceptable salt is a hydrochloride salt.

Atomoxetine hydrochloride can be prepared by adding a base to a mixture of (R)-(−)-tomoxetine (S)-(+)-mandelate and an organic solvent, followed by adding HCl, to obtain atomoxetine HCl.

Moreover, the present invention provides a process for preparing a pharmaceutical composition comprising R(−)-tomoxetine (atomoxetine) or a pharmaceutically acceptable salt thereof, which comprises bringing R(−)-tomoxetine (atomoxetine) or a pharmaceutically acceptable salt thereof into contact with one or more pharmaceutically acceptable carriers or excipients.

EXAMPLES

Achiral HPLC Analysis
Instrument: HPLC Hewlett Packard VWD detector HP 1100
Column: YMC ODS-AQ 250 mm×4.6 mm (i.d.) cod. AQ-303
Mobile phase: $NaH_2PO_4$ 0.02M pH 3 buffer—Acetonitrile gradient
Flow: 1.5 ml/min
Temperature: 40° C.
Wavelength: 215 nm Chiral HPLC Analysis
Instrument: HPLC Hewlett Packard VWD detector HP1100
Column: CHIRACEL OD-R cellulose tris (3,5-dimethylphenylcarbanate)
250 mm×4.60 mm×10 mm (Daicel Chemicals cat. N° DAIC14625)
Mobile phase: $KPF_6$ 100 mM/Acetonitrile—60/40
Flow: 0.8 ml/min
Temperature: 35° C.
Wavelength: UV, 215 nm Example 1

(R,S)-N-methyl-3-(2-methylphenoxy)-3-phenylpropylamine (Tomoxetine Synthesis)

1100 g (14.1 mol) of dimethylsulfoxide, 200 g (1.21 mol) of N-methyl-3-hydroxy-3-phenylpropylamine and 221 g (3.63 mol) of potassium hydroxide (bulk industrial grade, 92.1% assay) were heated under stirring at 110° C., then the mixture was concentrated by vacuum distillation until about 130 g of solvent were removed. The mixture was allowed to cool to 80° C., then 400 g (3.63 mol) of 2-fluorotoluene were added. The mixture was heated to reflux (145° C.-147° C.) for one hour, and then allowed to cool to about 90° C. 1000 ml of water and 1000 ml of toluene were added. The mixture was stirred for some minutes, at which time the phases were separated. The aqueous phase was extracted with 2×200 ml of toluene. The organic phases were collected and washed with 3×200 ml of water. Final organic phase weight: 1700 g. Tomoxetine content: 16.83% by weight (HPLC assay). Yield: 92.7%.

Example 2

(R)-(−)-Tomoxetine (S)-(+)-Mandelate (Tomoxetine Optical Resolution)

A solution in toluene of crude racemic tomoxetine (276.13 g, 1.081 mol, by HPLC assay) prepared as described in example 1 was concentration in vacuo to remove water. The residue was taken up with 2025 ml of toluene and 26 ml of methanol. To the obtained solution 94 g (0.618 mol) of (S)-(+)-mandelic acid were added at 25° C. All solids were solubilized by heating to 65°-70° C., and then crude mandelate salt was crystallized on cooling. The solid was isolated by filtration at 5°-10° C., washed with about 300 ml of toluene and dried in vacuo. Weight: 178 g. Tomoxetine content: 63.2% by weight (HPLC assay). Yield: 43.15%. Crude mandelate salt (R)-(−)-tomoxetine enantiomeric ratio: R/S is about 95/5 (by chiral HPLC).

163 g of the obtained crude mandelate salt was re-crystallized from 489 ml of toluene and 49 ml of methanol as follows: the salt was solubilized by heating to 65°-70° C., then (R)-(−)-tomoxetine (S)-(+)-mandelate was crystallized on cooling, isolated by filtration at 5°-10° C., washed with about 2×90 ml of toluene and dried in vacuum. Weight: 153 g. Tomoxetine content: 63.97% by weight (HPLC assay). Yield: 38.7% from racemic tomoxetine. (R)-(−)-tomoxetine (atomoxetine) enantiomeric ratio: R/S>99/1 (by chiral HPLC).

Example 3

(R)-(−)-Tomoxetine (S)-(+)-Mandelate (Tomoxetine Optical Resolution)

To 26.5 g of crude racemic Tomoxetine (0.104 mol, by HPLC assay) in toluenic solution (from example 2) 1.6 ml of methanol and 9.6 g (0.063 mol) of (S)-(+)-mandelic acid were added at 25° C. All solids were solubilized by heating to 65°-70° C., then crude mandelate salt was crystallized on cooling. The salt was isolated by filtration at 5°-10° C., washed with about 30 of toluene and dried in vacuum. Weight: 16.4 g. Tomoxetine content: 64.35% by weight (HPLC assay). Yield: 40% from racemic Tomoxetine. Crude mandelate salt (R)-(−)-tomoxetine enantiomeric ratio: R/S is about 97/3 (by chiral HPLC).

Example 4

(R)-(−)-Tomoxetine (S)-(+)-Mandelate (Tomoxetine Optical Resolution)

To a suspension of (S)-(+)-mandelic acid (10.72 g; 0.070 mol) in water (10 ml) 9.86 g (0.0739 mol) of 30% aqueous sodium hydroxide were added and the mixture was heated to 50-60° C. until complete dissolution. The resulting clear aqueous solution was dropped over a solution of crude racemic tomoxetine acetate in toluene, obtained by addition of glacial acetic acid (7.40 g; 0.123 mol) to a solution in toluene of crude racemic tomoxetine (30 g, 0.117 mol, by HPLC assay), prepared on its turn as described in Example 1. During the addition, temperature was raised to 35° C.; the biphasic system was then heated under vigorous stirring to 40° C. and then it spontaneously cooled to 20° C. The resulting suspension was then stirred at 20° C. for one hour, filtered and washed twice with toluene (30 ml each). The solid was dried at 50° C. under vacuum. (R)-(−)-tomoxetine mandelate 18.24 g; enantiomeric ratio: R/S 97: 3 (by chiral HPLC). Yield: 38.1%.

Example 5

Racemization of Unwanted Enantiomer

About 310 ml of toluenic solvent mixture ("mother liquors") from optical resolution (Examples 2-4) were washed with about 50 ml of 2% aqueous sodium hydroxide, and then concentrated under vacuum. The oily residue weighed 72.6 g and contained 51.29 g (0.20 mol) of tomoxetine (HPLC assay). 550 g (7.03 mol) of DMSO and 36.7 g (0.60 mol) of potassium hydroxide (bulk industrial grade, 92.1% assay) were added to the concentrate and the mixture was heated between 85° C. and 90° C. until optical rotation of the mixture decreased to 0.00 (3 hours). Heating was stopped, 300 ml of water and 300 ml of toluene were added. The mixture was stirred for some minutes, and then phases were separated. The aqueous phase was extracted with 50 ml of toluene. The organic phases were collected and washed with 3×80 ml of water, then concentrated under vacuum. Residue weight: 64.23 g. Tomoxetine content: 49.07 g (0.19 mol) (HPLC assay).

The residue was taken up with 392 ml of toluene and 2.9 ml of methanol, and then 17.15 g (0.115 mol) of (S)-(+)-mandelic acid were added to the obtained solution at 25° C. All solids were solubilized by heating to 65°-70° C. The solution was cooled, crude mandelate salt crystallized, was isolated by filtration at 5°-10° C., washed with about 2×40 ml of toluene and dried in vacuo. Weight: 33.6 g. Tomoxetine content: 62.9% by weight (HPLC assay). Yield: 41.2%. Crude mandelate salt (R)-(−)-Tomoxetine enantiomeric ratio: R/S is about 95/5 (by chiral HPLC).

Example 6

(R)-(−)-N-methyl-3-(2-methylphenoxy)-3-phenyl-propylamine hydrochloride (Atomoxetine Hydrochloride)

45 g (0.110 mol) of (R)-(−)-tomoxetine (S)-(+)-mandelate were mixed under stirring with 225 ml of toluene and 225 ml of water. Keeping the temperature at about 40° C. by means of gentle heating, 21 g (about 0.16 mol) of 30% aqueous sodium hydroxide were added. The phases were then separated. The organic phase was washed with 100 ml of 1% aqueous sodium hydroxide, then filtered on paper and concentrated in vacuum to give 29.67 g of an oil containing 26.8 g of tomoxetine (by HPLC assay).

23.5 g of the oil were dissolved in 211 ml of ethyl acetate under stirring then, keeping temperature between 12° C. and 18° C. by means of water-ice bath cooling; gaseous hydrogen chloride was bubbled into the solution until acid reaction of litmus paper. The hydrochloride then crystallized. The obtained suspension was stirred at about 15° C. for one hour, then the solid was collected by filtration, washed with ethyl acetate and dried in vacuo. Tomoxetine hydrochloride content: >99% by HPLC assay. Weight: 24.3 g (0.0832 mol). Yield: 95%. Atomoxetine hydrochloride enantiomeric ratio: R/S>99/1 (by chiral HPLC).

Having thus described the invention with reference to particular preferred embodiments and illustrative examples, those in the art may appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. All references mentioned herein are incorporated in their entirety.

We claim:

1. A process for the preparation of (R)-(−)-tomoxetine (S)-(+)-mandelate comprising:
   a) providing a reaction mixture comprising tomoxetine racemate, a $C_{1-4}$ alcohol, an aromatic solvent, and (S)-(+)-mandelic acid;
   b) heating the reaction mixture to a temperature of about 60° C. to about 80° C.; and
   c) crystallizing (R)-(−)-tomoxetine (S)-(+)-mandelate from the reaction mixture.

2. The process of claim 1 wherein the mixture is heated in step b) to a temperature of about 65° C. to about 70° C.

3. The process of claim 1 wherein R-(−)-tomoxetine (S)-(+)-mandelate is crystallized at a temperature of about −5° C. to about 20° C.

4. The process of claim 3 wherein R-(−)-tomoxetine (S)-(+)-mandelate is crystallized at a temperature of about 0° C.

5. The process of claim 1 further comprising recrystallization of R-(−)-tomoxetine (S)-(+)-mandelate obtained in step c).

6. The process of claim 5 wherein the R-(−)-tomoxetine (S)-(+)-mandelate is recrystallized in a solution of an aromatic solvent and a $C_{1-4}$ alcohol.

7. The process of any one of claims 1 and 6 wherein the $C_{1-4}$ alcohol is methanol.

8. The process of any one of claims 1 and 6 wherein the aromatic solvent is toluene.

9. A process for the preparation of (R)-(−)-tomoxetine (S)-(+)-mandelate comprising:
   a) combining, at a temperature of about 40° C. to about 60° C., (S)-(+)-mandelic acid in an aqueous basic solution, tomoxetine racemate, an aromatic solvent and acetic acid, to obtain a reaction mixture;
   b) maintaining the reaction mixture for at least one hour to obtain (R)-(−)-tomoxetine (S)-(+)-mandelate; and
   c) recovering (R)-(−)-tomoxetine (S)-(+)-mandelate from the reaction mixture.

10. The process of claim 9 wherein the aromatic solvent is toluene.

11. The process of claim 9 wherein the aqueous basic solution contains sodium hydroxide, potassium hydroxide, cesium hydroxide, calcium hydroxide or ammonium hydroxide.

12. The process of claim 11 wherein the aqueous basic solution contains sodium hydroxide.

13. The process of claim 9, wherein the reaction mixture in step b) is maintained at a temperature of about −5° C. to about 20° C.

14. The process of claim 13, wherein said mixture is maintained at a temperature of about 0° C.

15. A process for preparing racemic tomoxetine which comprises:
   a) providing a mixture comprising (S)-(+)-tomoxetine, an aprotic dipolar solvent and a base having a highly ionic counter ion,
   b) heating the mixture to a temperature of about 80° C. to about 150° C., and
   c) maintaining the mixture for at least 3 hours to obtain racemic tomoxetine.

16. The process of claim 13, which includes adding (S)-(+)-mandelic acid to the mixture of step c) and then crystallizing (R)-(−)-tomoxetine (S)-(+)-mandelate from the resulting mixture.

17. The process of claim 15 where (S)-(+)-tomoxetine is washed with a base and concentrated prior to step a).

18. The process of claim 15, wherein the mixture in step b) is heated to a temperature of about 85° C. to about 90° C.

19. The process of claim 15, wherein the aprotic dipolar solvent is selected from the group consisting of DMF, dimethylacetamide, 1,3-dimethyl-2-imidazolinone and DMSO.

20. The process of claim 19, wherein the aprotic dipolar solvent is DMSO.

21. The process of claim 15, wherein the base in step a) is potassium hydroxide.

22. A process for the preparation of atomoxetine or a pharmaceutically acceptable salt thereof comprising:
   a) providing a reaction mixture comprising tomoxetine racemate, a $C_{14}$ alcohol, an aromatic solvent, and (S)-(+)-mandelic acid;
   b) heating the reaction mixture to a temperature of about 60° C. to about 80° C.;
   c) crystallizing (R)-(−)-tomoxetine (S)-(+)-mandelate from the reaction mixture; and
   d) converting the obtained (R)-(−)-tomoxetine (S)-(+)-mandelate into atomoxetine or a pharmaceutically acceptable salt thereof.

23. A process for the preparation of atomoxetine or a pharmaceutically acceptable salt thereof comprising:
   a) combining, at a temperature of about 40° C. to about 600° C., (S)-(+)-mandelic acid in an aqueous basic solution, tomoxetine racemate, an aromatic solvent and acetic acid, to obtain a reaction mixture;
   b) maintaining the reaction mixture for at least one hour to obtain (R)-(−)-tomoxetine (S)-(+)-mandelate;
   c) recovering (R)-(−)-tomoxetine (S)-(+)-mandelate from the reaction mixture; and
   d) converting the obtained (R)-(−)-tomoxetine (S)-(+)-mandelate into atomoxetine or a pharmaceutically acceptable salt thereof.

24. The process of any one of claims 22 and 23, wherein the pharmaceutically acceptable salt is hydrochloride.

25. A process for preparing a pharmaceutical composition comprising R(−)-tomoxetine (atomoxetine) or a pharmaceutically acceptable salt thereof, which comprises:
   a) providing a reaction mixture comprising tomoxetine racemate, a $C_{1-4}$ alcohol, an aromatic solvent, and (S)-(+)-mandelic acid;
   b) heating the reaction mixture to a temperature of about 60° C. to about 80° C.;
   c) crystallizing (R)-(−)-tomoxetine (S)-(+)-mandelate from the reaction mixture;

d) converting the obtained (R)-(−)-tomoxetine (S)-(+)-mandelate into R(−)-tomoxetine, or a pharmaceutically acceptable salt thereof; and e) bringing the R(−)-tomoxetine (atomoxetine) or a pharmaceutically acceptable salt thereof formed in step d) into contact with one or more pharmaceutically acceptable carriers or excipients.

26. A process for preparing a pharmaceutical composition comprising R(−)-tomoxetine (atomoxetine) or a pharmaceutically acceptable salt thereof, which comprises:

a) combining, at a temperature of about 40° C. to about 60° C., (S)-(+)-mandelic acid in an aqueous basic solution, tomoxetine racemate, an aromatic solvent and acetic acid, to obtain a reaction mixture;

b) maintaining the reaction mixture for at least one hour to obtain (R)-(−)-tomoxetine (S)-(+)-mandelate;

c) recovering (R)-(−)-tomoxetine (S)-(+)-mandelate from the reaction mixture;

d) converting the obtained (R)-(−)-tomoxetine (S)-(+)-mandelate into R(−)-tomoxetine or a pharmaceutically acceptable salt thereof; and e) bringing the R(−)-tomoxetine, or pharmaceutically acceptable salt thereof, formed in step d) into contact with one or more pharmaceutically acceptable carriers or excipients.

* * * * *

UNITED STATES PATENT AND TRADEMARK OFFICE
CERTIFICATE OF CORRECTION

PATENT NO. : 7,317,127 B2
APPLICATION NO. : 11/170379
DATED : January 8, 2008
INVENTOR(S) : Casteli et al.

It is certified that error appears in the above-identified patent and that said Letters Patent is hereby corrected as shown below:

Column 2
Line 34, change "butyllithium" to --*n*-butyllithium--

Column 5
Line 53, change "R(-)-tomoxetine" to --(R)-(-)-tomoxetine--
Lines 53-54, change "S-(+)-mandelate" to --(S)-(+)-mandelate--
Line 62, change "R(-)-tomoxetine" to --(R)-(-)-tomoxetine--
Line 64, change "R(-)-tomoxetine" to --(R)-(-)-tomoxetine--

Column 6
Line 40, change "Achiral HPLC Analysis" to --Achiral HPLC Analysis--
Line 49, change "Chiral HPLC Analysis" to --Chiral HPLC Analysis--
Line 61, change "Example 1" to --Example 1--
Lines 63-64, change "(R,S)-N-methyl-3-(2-methylphenoxy)-3-phenylpropylamine (Tomoxetine Synthesis)" to
--*(R,S)-N-methyl-3-(2-methylphenoxy)-3-phenylpropylamine (Tomoxetine synthesis)*--

Column 7
Line 16, change "Example 2" to --Example 2--
Lines 18-19, change "(R)-(-)-Tomoxetine (S)-(+)-Mandelate (Tomoxetine Optical Resolution)" to --*(R)-(-)-Tomoxetine (S)-(+)-Mandelate (Tomoxetine Optical Resolution)*--
Line 23, change "concentration" to --concentrated--
Line 23, change "in vacuo" to --*in vacuo*--
Line 25, change "obtained solution 94g" to --obtained solution, 94g--
Line 26, change "were" to --was--
Line 44, change "Example 3" to --Example 3--
Lines 46-47, change "(R)-(-)-Tomoxetine (S)-(+)-Mandelate (Tomoxetine Optical Resolution)" to --*(R)-(-)-Tomoxetine (S)-(+)-Mandelate (Tomoxetine Optical Resolution)*--
Line 61, change "Example 4" to --Example 4--
Lines 63-64, change "(R)-(-)-Tomoxetine (S)-(+)-Mandelate (Tomoxetine Optical Resolution)" to --*(R)-(-)-Tomoxetine (S)-(+)-Mandelate (Tomoxetine Optical Resolution)*--

UNITED STATES PATENT AND TRADEMARK OFFICE
CERTIFICATE OF CORRECTION

PATENT NO. : 7,317,127 B2
APPLICATION NO. : 11/170379
DATED : January 8, 2008
INVENTOR(S) : Casteli et al.

It is certified that error appears in the above-identified patent and that said Letters Patent is hereby corrected as shown below:

Column 8
Line 17, change "Example 5" to --Example 5--
Line 19, change "Racemization of Unwanted Enantiomer" to --*Racemization of Unwanted Enantiomer*--
Line 49, change "Example 6" to --Example 6--
Lines 51-53, change "(R)-(-)-N-methyl-3-(2-methylphenoxy)-3-phenyl-propylamine hydrochloride (Atomoxetine Hydrochloride)" to
--*(R)-(-)-N-methyl-3-(2-methylphenoxy)-3-phenyl-propylamine hydrochloride (Atomoxetine Hydrochloride)*--

Column 9
Line 33, change "R-(-)-tomoxetine" to --(R)-(-)-tomoxetine--
Line 36, change "R-(-)-tomoxetine" to --(R)-(-)-tomoxetine--

Column 11
Line 2, change "R(-)-tomoxetine" to --(R)-(-)-tomoxetine--
Line 4, change "R(-)-tomoxetine" to --(R)-(-)-tomoxetine--
Line 9, change "R(-)-tomoxetine" to --(R)-(-)-tomoxetine--

Column 12
Line 7, change "R(-)-tomoxetine" to --(R)-(-)-tomoxetine--
Line 9, change "R(-)-tomoxetine" to --(R)-(-)-tomoxetine--

Signed and Sealed this

First Day of September, 2009

David J. Kappos
*Director of the United States Patent and Trademark Office*